(12) United States Patent
Clagg et al.

(10) Patent No.: US 11,136,330 B2
(45) Date of Patent: Oct. 5, 2021

(54) SYNTHESIS OF LABELED IMIDAZO[1,2-A]PYRIMIDINES

(71) Applicant: Genentech, Inc., South San Francisco, CA (US)

(72) Inventors: Kyle Bradley Pascual Clagg, San Francisco, CA (US); Nicholas Andrew White, San Francisco, CA (US); Haiming Zhang, San Mateo, CA (US); Francis Gosselin, San Mateo, CA (US); William Nack, Glenview, IL (US); Paul D. O'Shea, Princeton, NJ (US)

(73) Assignee: Genentech, Inc., South San Francisco, CA (US)

(*) Notice: Subject to any disclaimer, the term of this patent is extended or adjusted under 35 U.S.C. 154(b) by 0 days.

(21) Appl. No.: 16/869,475

(22) Filed: May 7, 2020

(65) Prior Publication Data

US 2020/0354369 A1  Nov. 12, 2020

Related U.S. Application Data

(60) Provisional application No. 62/845,840, filed on May 9, 2019, provisional application No. 62/937,069, filed on Nov. 18, 2019.

(51) Int. Cl.
C07D 487/04 (2006.01)
C07F 9/24 (2006.01)

(52) U.S. Cl.
CPC .......... C07D 487/04 (2013.01); C07F 9/2454 (2013.01)

(58) Field of Classification Search
CPC .......................... C07D 487/04; C07F 9/2454
See application file for complete search history.

(56) References Cited

U.S. PATENT DOCUMENTS 8,491,869 B2 * 7/2013 Gangadharmath .. C07D 277/62
424/1.89
8,691,187 B2   4/2014 Szardenings et al.
(Continued)

FOREIGN PATENT DOCUMENTS

WO   2015/173225 A1   11/2015
WO   2016/066490 A1    5/2016

OTHER PUBLICATIONS

Bajwa and Sykes et al., "Synthesis and Structure of Some Azolo [a] pyrimidines, 2,6,7,8—Tet ra hydro—1 H-cyclopenta[e]azolo[a]pyrimidines, 6,7-Dihydro-5H-cyclopenta[f]—azolo[a]pyrimidines, 7,8-Dihydro-G~-cyclopenta[f]-s-triazolo[4,3-b]pyridazine, 5,6,7,8-Tetrahydro-azolo [b]quinazolines, 6,7,8,9- Tetra hydroazolo[ a]quinazolines, and 7,8,9,1 O—Tetrahydro-s-triazolo[3,4-a] phthalazine" J.C.S. Perkin I:3085-3094 ( 1979).

(Continued)

*Primary Examiner* — Erich A Leeser
(74) *Attorney, Agent, or Firm* — Genentech, Inc.; Richard G. A. Bone

(57) ABSTRACT

A method of synthesizing

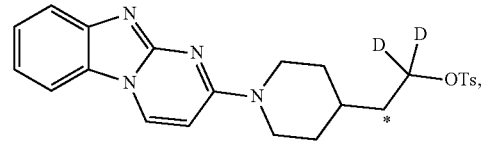

comprising a step of making an imidazo-pyrimidine compound by coupling a first compound of formula (II) with a second compound of formula (III)

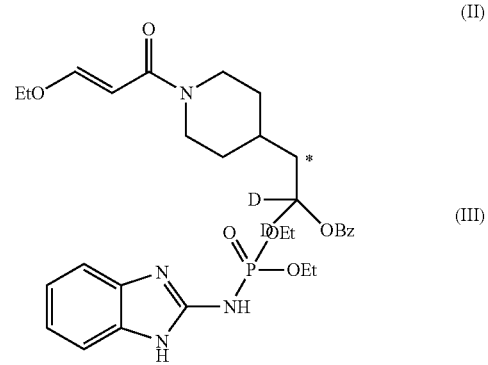

Followed by a deprotection and tosylation step. The methods are able to produce an isotopically substituted molecule having upwards of 95% purity relative to non-isotopically substituted molecules.

The invention further comprises compounds of formula:

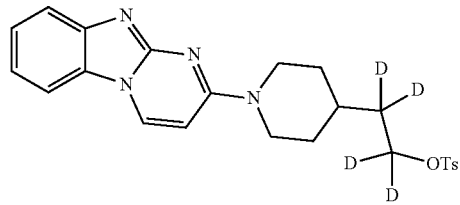

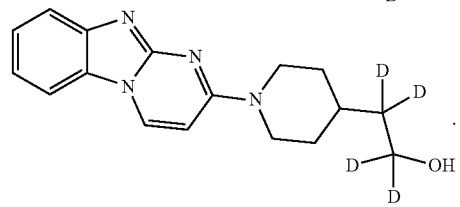

38 Claims, 2 Drawing Sheets

(56) References Cited

U.S. PATENT DOCUMENTS

| 10,076,581 | B2 | 9/2018 | Marik et al. |
| 10,675,367 | B2 | 6/2020 | Marik et al. |
| 2011/0182812 | A1 | 7/2011 | Szardenings et al. |
| 2020/0369670 | A1 | 11/2020 | Clagg et al. |

OTHER PUBLICATIONS

Dawood et al., "Synthesis of Spiro-pyrazole-3,3'-thiopyrano[2,3-b]pyridines and Azolo[a]pyrido[2', 3':5,6]thiopyrano[3,4-d]pyrimidines as New Ring Systems with Antifungal and Antibacterial Activities" J. Heterocyclic Chem. 42:221-225 ( 2005).

Fang et al., "One-Pot Synthesis of Benzo[4,5]imidazo[1,2-a]quinazoline Derivatives via Facile Transition-Metal-Free Tan dem Process" ACS Comb. Sci. 16:328-332 ( 2014).

Gao, M., et al., "Concise and high-yiel synthests of T808 and T808P for radiosynthesis of 18F-T808, a PET tau tracer for Alzheimer's disease" Bioorg Med Chem Lett 24(1):254-257 (Jan. 1, 2014).

Goryaeva et al., "Synthesis of Pyrimido[1,2-a]benzimidazoles from Ethyl 2-Ethoxymethylidene-3-oxo-3-(polyfluoroalkyl)propionates" Russian J. Org. Chem. 46(3):432-438 ( 2010).

Iaroshenko et al., "4-Chloro-3-(trifluoroacetyl)- and 4-chloro-3-(methoxalyl)coumarins as novel and efficient building blocks for the regioselective synthesis of 3,4-fused coumarins" Tetrahedron 67:7946-7955 ( 2011).

International Search Report and Written Opinion for PCT/EP2020/031953 dated Jul. 20, 2020.

Kunstlinger and Breitmaier et al., "Imidazo[1,2-a]pyrimidine from 2-aminoimidazoles and 3-alkoxyacroleins" Synthesis:161-162 ( 1983).

White, N., et at, "Phosphoramidates as Steering Elements for Highly Selective Access to Complementary Imidazo[1,2-a]pyrimidine Isomers" Org Lett 21(23):9527-9531 (Nov. 18, 2019)

Zanatta et at, "Synthesis and Characterization of Some Novel 2-(Trifluoromethyl)pyrimido-[1,2-a]benzimidazoles and Pyrimido[1,2-a]benzimidazol-2H)—ones of Biological Interest" Synthesis 14:2305-2312 ( 2006).

\* cited by examiner

SYNTHESIS OF LABELED IMIDAZO[1,2-A]PYRIMIDINES

CLAIM OF PRIORITY

This application claims benefit of priority under 35 U.S.C. § 119(e) to U.S. provisional application Ser. Nos. 62/845,840, filed May 9, 2019, and 62/937,069, filed Nov. 18, 2019, both of which are incorporated herein by reference in their entirety.

TECHNICAL FIELD

The technology described herein generally relates to organic synthesis, and more particularly relates to synthetic pathways to molecules that are isotopically labeled and are used as imaging agents in positron emission tomography.

BACKGROUND

Neurofibrillary tangles (NFTs) are deposits in the brain that are believed to be a hallmark of several neuropathologies, including Alzheimer's disease (AD). NFT plaques are comprised of aggregated hyperphosphorylated tau protein. The tau protein is associated with cytoskeleton and is involved in the transport of vesicles along microtubules in neurons. Under pathological conditions, tau is hyperphosphorylated and forms beta-sheet aggregates with fibrillar appearances similar to Aβ in senile plaques. Some tau-targeted therapies aim to slow disease progression by interfering with cell-to-cell transfer of soluble tau oligomers. If a patient's tau burden can be reliably monitored, currently and over time, then disease progression can be better understood and such therapeutic approaches can be improved. Tau-specific positron emission tomography (PET) imaging biomarkers can non-invasively monitor disease progression as well as provide a direct measure of tau-targeted agent efficacy and confirmation of its mechanism of action in clinical trials (see, e.g., Mathis, C. A.; Klunk, W. E., *Neuron*, (2013), 79 (6), 1035-7; and Jensen, J. R., et al., *J. Alzheimer's Disease*, (2011), 26 Suppl. 3, 147-57).

One promising tau-specific PET imaging biomarker is a substituted benzo[4,5]imidazo[1,2-a]pyrimidin-2-amine that is both deuterated as well as labeled by a radio-isotope. For clinical applications, the radio-isotope $^{18}$F is introduced into a precursor molecule immediately prior to administration of the compound to a patient. Correspondingly, an efficient synthesis of the precursor is particularly desirable because the precursor must be commercially available in large quantities that are ready for labeling.

The benzo[4,5]imidazo[1,2-a]pyrimidin-2-amine structural element has also found utility in a number of other PET imaging agents that target tau protein plaques, and has also been incorporated into investigational tau degrader molecules. Additionally, this scaffold has been used as a PET imaging agent for the identification of other proteins associated with neurodegenerative conditions such as Huntington's disease. More generally, the benzo[4,5]imidazo[1,2-a]pyrimidine motif has been incorporated into molecules which have shown anti-neurodegenerative, anti-hypertensive, anti-microbial, and antiviral activity.

Traditionally, benzo[4,5]imidazo[1,2-a]pyrimidine derivatives have been accessed via the condensation of amino-imidazoles with enones or enals bearing a leaving group in the β-position. While this approach generally provides imidazo-pyrimidine products in high yield and good isomeric selectivity, the scope of available substrates is limited to α,β-unsaturated aldehydes and ketones. To enable more efficient access to functionalized imidazo[1,2-a]pyrimidin-amines, other methods are needed.

The discussion of the background herein is included to explain the context of the technology. This is not to be taken as an admission that any of the material referred to was published, known, or part of the common general knowledge as at the priority date of any of the claims found appended hereto.

Throughout the description and claims of the instant application the word "comprise" and variations thereof, such as "comprising" and "comprises", is not intended to exclude other additives, components, integers or steps.

SUMMARY

The instant disclosure addresses the synthesis of substituted imidazopyrimidine molecules, particularly a number that are deuterated at specific positions.

In particular, the disclosure comprises a coupling step that can make a substituted imidazo-pyrimidine in high yield.

Selective N-phosphorylation of aminoimidazoles results in a key steering element that controls isomeric selectivity in the condensation of β-ethoxy acrylamides and amino-imidazoles to furnish imidazo[1,2-a]pyrimidines. Conditions that provide highly selective (99:1) phosphorylation at the endo- or exocyclic nitrogen are disclosed. Either the 2-amino or 4-amino isomer of the (benzo)imidazo[1,2-a]pyrimidine products can be isolated in 64-95% yield.

The disclosure further includes a compound of formula (V):

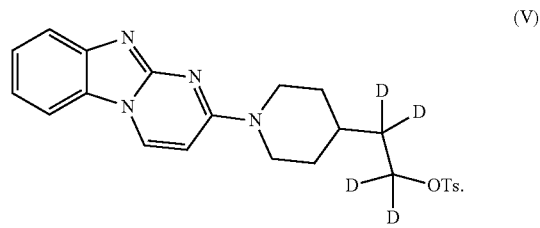 [SMILES: [2H]C([2H])(OS(=O)(=O)c1ccc(C)cc1)C([2H])([2H])C1CCN(c2ccn3c(n2)nc2ccccc23)CC1]

(V)

In particular, compound (V) may have a deuterium enrichment factor of 3,000 or greater at each of the positions shown as occupied by a deuterium atom.

The disclosure further includes a compound of formula (VI):

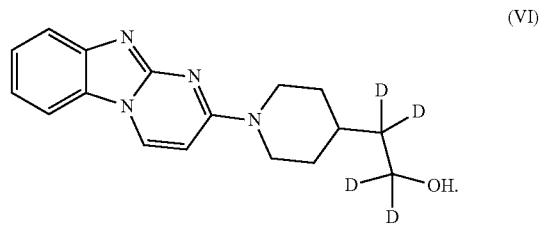 [SMILES: [2H]C([2H])(O)C([2H])([2H])C1CCN(c2ccn3c(n2)nc2ccccc23)CC1]

(VI)

In particular, compound (VI) may have a deuterium enrichment factor of 3,000 or greater at each of the positions shown as occupied by a deuterium atom.

The disclosure further comprises a method of synthesizing the compound of formula (I),

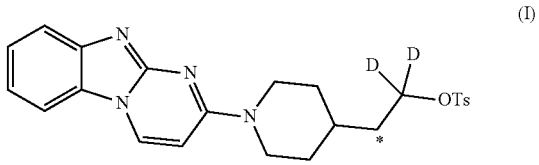 [SMILES: [2H]C([2H])(CC1CCN(c2ccn3c(n2)nc2ccccc23)CC1)OS(=O)(=O)c1ccc(C)cc1]
(I)

the method comprising:
at least a step of coupling a compound of formula (II) with a compound of formula (III)

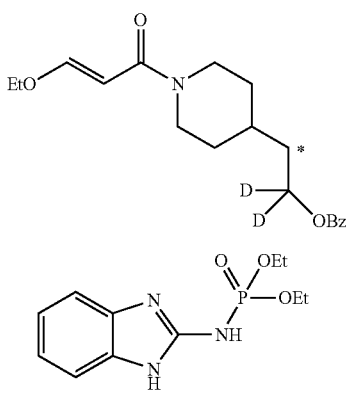

in the presence of POCl$_3$ and Et$_3$N in a non-aqueous solvent to give a first precursor (I-P1).

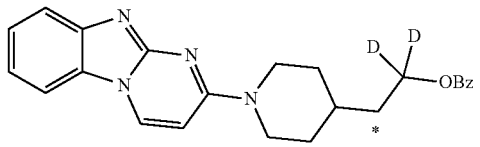
(I-P1)

The synthesis further comprises removing the benzoate group in I-P1 to give a second precursor (I-P2); and

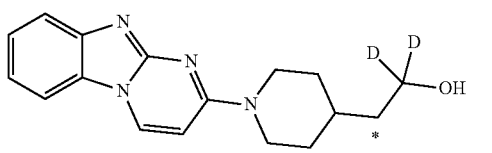
(I-P2)

replacing the hydroxyl group in I-P2 by a tosyl group to give compound (I), wherein, in formulae (I), (II), (I-P1) and (I-P2), the carbon atom labeled (*) is optionally doubly-deuterated.

DETAILED DESCRIPTION

Figure 1:
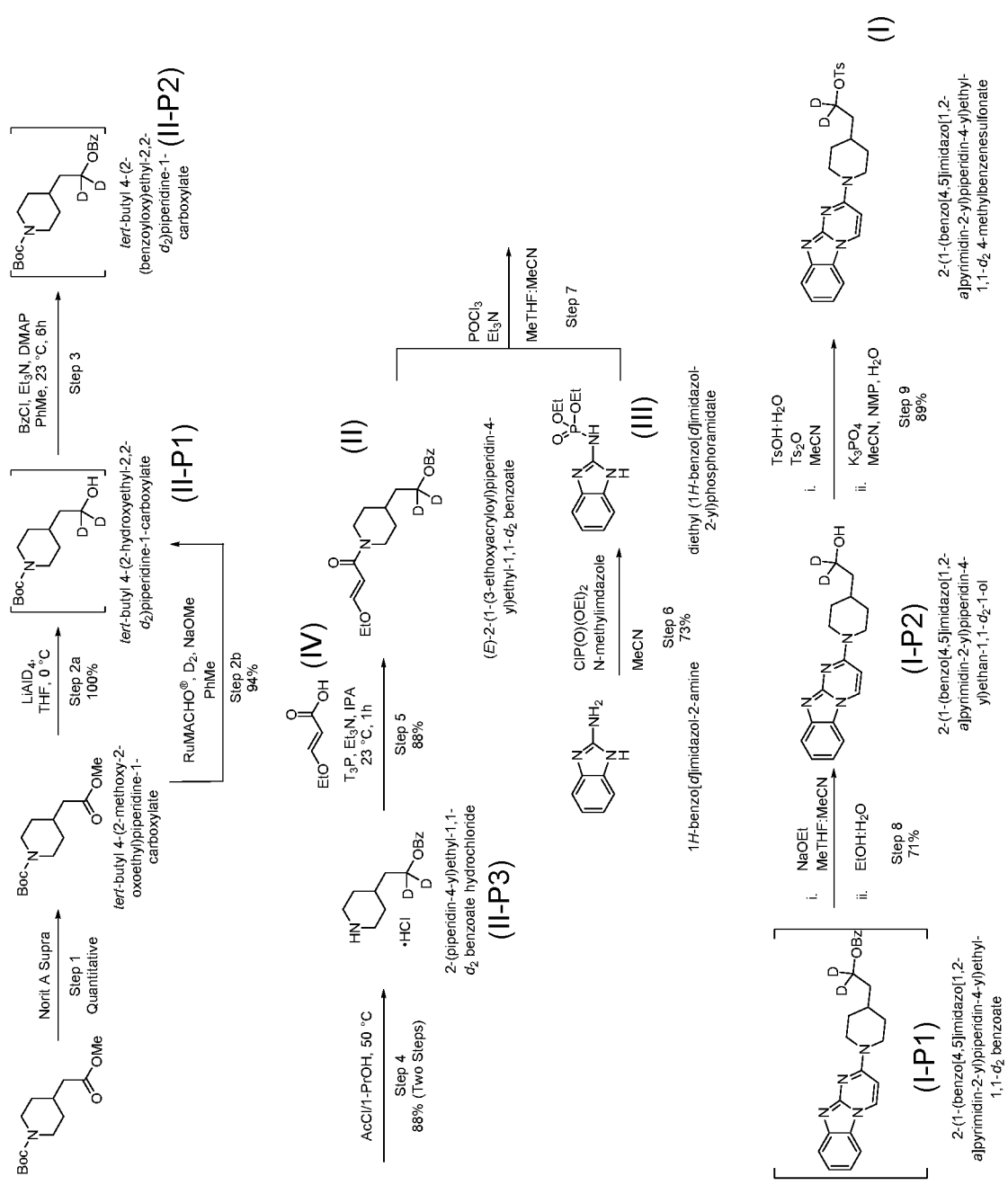
FIG. 1 shows a first flow-chart of a process as described herein.

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described. In the event that one or more of the incorporated literature, patents, and similar materials differs from or contradicts this application, including but not limited to defined terms, term usage, described techniques, or the like, this application controls.

Unless otherwise defined, all technical and scientific terms used herein have the same meaning as commonly understood by one of ordinary skill in the art to which this invention belongs. The nomenclature used in this application is based on the *ACS Style Guide* and the *The Journal of Organic Chemistry* list of "Standard Abbreviations and Acronyms" (both published by the American Chemical Society, Washington, D.C.), as well as on IUPAC systematic nomenclature, unless indicated otherwise.

Definitions

Chemical elements are identified in accordance with the Periodic Table of the Elements, CAS version, Handbook of Chemistry and Physics, 75th Ed.

Unless otherwise stated, the compounds include enantiomeric, diastereomeric and geometric (or conformational) isomeric forms of a given structure unless the structure is otherwise intended to be limited. For example, the R and S configurations for each asymmetric center, Z and E double bond isomers, Z and E conformational isomers, single stereochemical isomers, as well as enantiomeric, diastereomeric, and geometric (or conformational) mixtures are included. Unless otherwise stated, all tautomeric forms of structures depicted herein are also included.

It is to be understood that when a compound or Example herein is shown as a specific salt, the corresponding free-base, as well as other salts of the corresponding free-base (including pharmaceutically acceptable salts of the corresponding free-base) are contemplated.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

Unless otherwise stated, structures depicted herein are also meant to include compounds that differ only in the presence of one or more isotopically enriched atoms in addition to any isotopically enriched atom that has been explicitly identified. For example, compounds, wherein the independent replacement or enrichment of one or more hydrogen by deuterium or tritium, carbon by $^{13}$C- or $^{14}$C carbon, nitrogen by a $^{15}$N nitrogen, sulfur by a $^{33}$S, $^{34}$S or $^{36}$S sulfur, or oxygen by a $^{17}$O or $^{18}$O oxygen are included.

Such compounds are useful, for example, as analytical tools, as probes in biological assays, or as therapeutic agents.

The term "deuterated" means that a hydrogen atom is replaced by a deuterium atom at a level above its natural abundance at one or more positions of a molecule. When a particular position is deuterated, it is understood that the abundance of deuterium at that position is substantially greater than the natural abundance of deuterium, which is 0.015%. A deuterated position typically has a minimum isotopic enrichment factor of at least 3000 (45% deuterium incorporation).

The term "isotopic enrichment factor" as used herein means the ratio between the isotopic abundance and the natural abundance of a specified isotope. In certain embodiments, a given position in a molecule has an isotopic enrichment factor of at least 3500 (52.5% deuterium incorporation), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). In some embodiments, 100% deuterium incorporation is achieved.

Deuterium can be incorporated into a compound of the present invention using a variety of known reagents and synthetic techniques. For example, deuterium can be incorporated into a compound of formula (I) using $LiAlD_4$ at an earlier stage in the synthesis that leads to compound (I). It can also be incorporated into a compound of formula (I) such as through reduction, catalytic hydrogenation or isotopic exchange using appropriate deuterated reagents such as deuterium gas $D_2$, and deuterated (or "heavy") forms of water such as HDO or $D_2O$.

As between chemical names and structures shown, if there are any discrepancies, the structure prevails.

As used herein, "a" or "an" means one or more, unless clearly indicated otherwise.

Compounds

The invention comprises compounds that are deuterated at four positions (often referred to by "d4" as a prefix to the compound name), as follows:

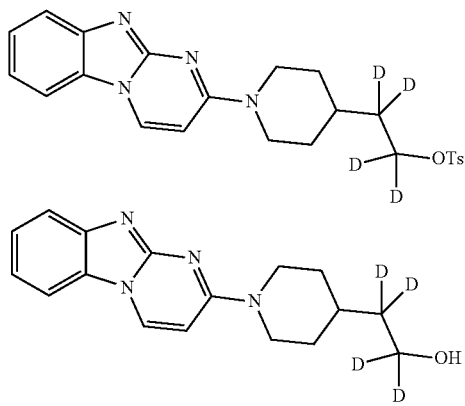

As described elsewhere herein, the invention further comprises methods of synthesis of such compounds.

It should be understood that "d4" means that each of the deuterated positions has an enrichment factor of at least 3000, and preferably at least 3500, and still more preferably at least 4000, and even more preferably at least 4500.

It should further be understood that, after synthesis, a d4-compound can be further purified to ensure that the enrichment factor at each of the deuterated positions is effectively at least 5000 or more.

Synthetic Methods

As described by way of specific synthetic schemes in the Examples that follow, the invention comprises a method of synthesizing a compound of formula (I):

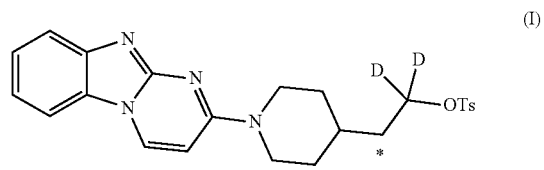

wherein the carbon atom labeled with a star (*) is optionally doubly-deuterated. In the instance that the carbon atom indicated (*) is doubly-deuterated, compound (I) is a d4-compound as described elsewhere herein.

The methods herein can obtain a di-deuterated ("d2") form at a purity of >95% D2/(D0+D1+D2)>95%, where Dn denotes a molecule having n of the designated hydrogens substituted by deuterium atoms). In preferred embodiments, the purity is at least 97% of the d2 form. The quality (i.e., isotopic enrichment factor) of lithium aluminum deuterate ($LiAlD_4$) is the principal driving force behind the actual purity of the compound obtained. A synthetic approach in which catalytic $D_2$ gas is used to introduce deuterium atoms into the molecule typically cannot produce more than 98% purity of the d2 form. Consequently the deuterium enrichment factor for each substituted position is typically in excess of 6333.3, and preferably in excess of 6400.

A method of synthesizing compounds of formula (I) comprises, in a first step, coupling an acrylamide compound of formula (II) with an amino-imidazole compound of formula (III)

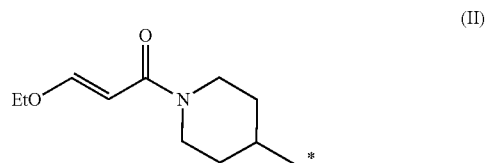

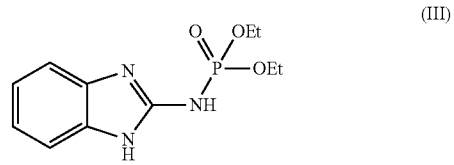

in the presence of $POCl_3$ and $Et_3N$ in a non-aqueous solvent to give a first precursor (I-P1)

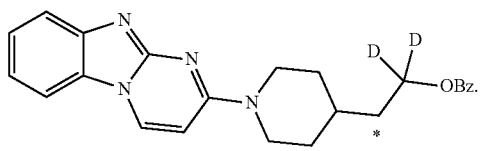

(I-P1)

This reaction provides the benzo[4,5]imidazo[1,2-a]pyrimidin-2-amine or (I-P1) with excellent selectivity over the alternative isomer, a benzo[4,5]imidazo[1,2-a]pyrimidin-4-amine.

It would be understood by those of skill in the art that a number of suitable choices of non-aqueous solvent for this step exist, and also that other reagents may be suitably identified to achieve the coupling. The group Bz in (II) and (I-P1) denotes carboxyphenyl (—C(=O)Ph).

In a second step, the benzoate group in (I-P1) is removed to give a second precursor (I-P2):

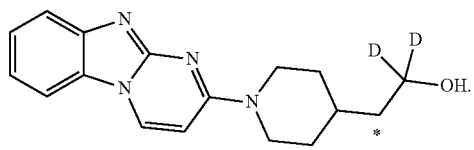

(I-P2)

This second step may occur in the presence of a base such as NaOH.

In a third step, the hydroxyl group in I-P2 is replaced by a tosyl group to give compound (I). Tosylation may optionally involve an acidification step after reacting (I-P2) with tosylate.

It is to be assumed that in formulae (II), (I-P1) and (I-P2), the carbon atom labeled (*) is also optionally doubly-deuterated. The reagents deployed to achieve the second and third steps may differ according to whether the carbon atom labeled (*) is doubly-deuterated.

In some embodiments, the compound of formula (II) is synthesized by a method comprising:
reacting

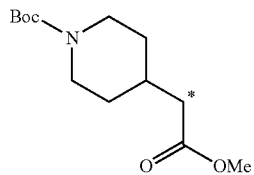 [SMILES: COC(=O)CC1CCN(C(=O)OC(C)(C)C)CC1]

with a first deuterating agent to produce

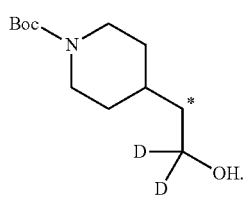

(II-P1)

The first deuterating agent can be LiAlD$_4$ or can be D$_2$ gas.

In a subsequent step, a benzoyl group is added to the hydroxyl group of (II-P1) to produce a further intermediate

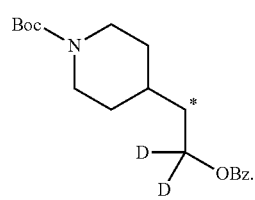

(II-P2)

In a further step, the Boc protecting group is removed from (II-P2) to produce a hydrochloride salt (II-P3)

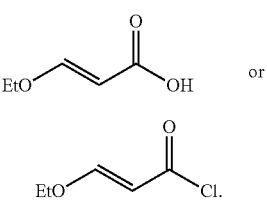

(II-P3)

A compound of formula (II) can be formed by reacting (II-P3) with

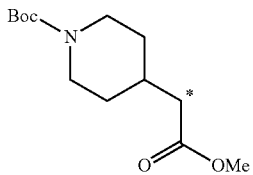 [SMILES: COC(=O)CC1CCN(C(=O)OC(C)(C)C)CC1]

(IV)

or (IVa)

In some embodiments, compound (IVa) is formed by reacting (IV) with SOCl$_2$.

In some embodiments, wherein the carbon atom labeled (*) in (II) is doubly deuterated, compound (II-P1) is created by reacting

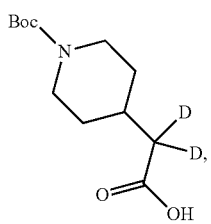

with a second deuterating agent to produce intermediate (II-P0)

(II-P0)

and reacting the first deuterating agent with (II-P0) to form (II-P1).

In some embodiments, the compound of formula (III) is synthesized by a method comprising: reacting

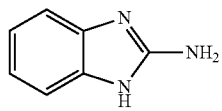

with PCl(O)(OEt)₂, N-methylimidazole, and MeCN.

In some embodiments, the phosphorylating agent, PCl(O)(OEt)₂ is formed in situ by reacting diethyl hydrogen phosphate with a chlorinating agent such as 1,3,5-trichloro-1,3,5-triazinane-2,4,6-trione.

One of skill in the art would appreciate that there are various ways to introduce a radio-isotope into a compound of formula (I) in order to make a tracer compound for use with imaging technology such as positron emission tomography. For example, compounds of formula (I) can be tritiated (labeled with one or more tritium atoms), or the tosylate function can be replaced by a $^{18}$F isotope, both according to methods known in the art.

EXAMPLES

Example 1: Synthesis of 2-(1-(benzo[4,5]imidazo[1,2-a]pyridin-3-yl)piperidin-4-yl)ethyl-1,1,2,2-d4 4-methylbenzenesulfonate Example 1 describes a representative synthesis of a tracer molecule deuterated at two positions including use of a step of conjugating an acrylamide with a phosphorylated imidazole. FIG. 1 shows the synthetic pathway of Example 1 in overview, including steps to prepare starting materials.

Step 1—Charcoal Treatment

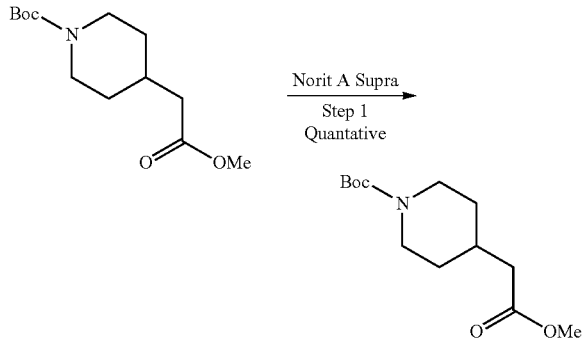

To a reactor under nitrogen equipped with overhead agitation was charged tert-butyl 4-(2-methoxy-2-oxoethyl)piperidine-1-carboxylate (600 g, 2.33 mol, 1.0 equiv) and MTBE (4800 mL). Once full dissolution of the oil was observed, Norit™ A Supra charcoal (120 g, 20 w %) was charged to the reactor and the jacket was warmed to 35-45° C. The mixture was held at this temperature for 2 h, cooled to 23° C., then filtered through a Büchner funnel containing 100.54 g of Celite®. The funnel was then washed with MTBE (1200 mL).

This procedure was repeated on another 600 g batch of tert-butyl 4-(2-methoxy-2-oxoethyl)piperidine-1-carboxylate and after filtration through Celite® and washing with MTBE (1200 mL), both solutions were combined then concentrated to dryness to obtain tert-butyl 4-(2-methoxy-2-oxoethyl)piperidine-1-carboxylate as a clear yellow oil (1137.89 g, 105.0%) in 97.33 A % HPLC purity.

Step 2a—Reduction (RuMACHO)

To a pressure reactor was charged tert-butyl 4-(2-methoxy-2-oxoethyl)piperidine-1-carboxylate (20 g, 77.72 mmol, 1.0 equiv), NaOMe (0.42 g, 7.77 mmol, 0.10 equiv), RuMACHO® (0.48 g, 0.78 mmol, 0.01 equiv), then PhMe (200 mL). The reactor was then sealed, the atmosphere evacuated under vacuum then backfilled with deuterium gas (20 atm) three times. The pressure reactor was then heated to 100° C. and stirred for 24 h. The reactor was then cooled to 23° C., filtered through short pad of silica gel, rinsed with PhMe, and concentrated under vacuum to afford tert-butyl 4-(2-hydroxyethyl-2,2-d₂)piperidine-1-carboxylate as a yellow oil (17.0 g, 94.5% corrected yield) in 100.0 A % HPLC purity.

Step 2b—Reduction (LiAlD₄)

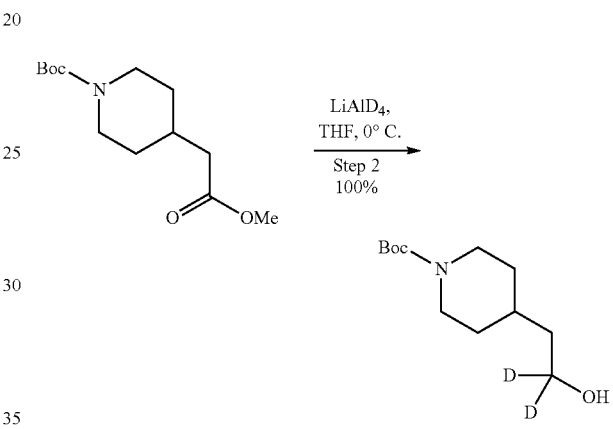

To a reactor under nitrogen equipped with overhead agitation was charged anhydrous THF (20.0 L) and tert-butyl 4-(2-methoxy-2-oxoethyl)piperidine-1-carboxylate (2020 g, 7.85 mol, 1.0 equiv). The reactor was then cooled to 0-5° C. over 1-2 h then LiAlD₄ (287.5 g, 6.85 mol, 0.87 equiv) was slowly charged in a portion-wise fashion. (Caution was appropriate as there was significant gas evolution.) Upon complete charging of the reagent, the reaction was stirred at 0-5° C. for 1 h. After reaction completion was confirmed, the reaction was quenched by slow addition of H₂O (287 mL) while maintaining the internal temperature to ≤15° C. (Caution was appropriate as there was significant gas evolution.) The reactor was then warmed to 20-25° C. and stirred for 30 min. An aqueous 4N NaOH solution (287 g, 250 mL) was charged to the reactor and the mixture was again stirred at 20-25° C. for 30 min. Lastly, H₂O (860 mL) was charged to the reactor and the mixture was again stirred at 20-25° C. for 30 min. The layers from the filtered mixture were then separated and the aqueous layer was discarded to waste. Na₂SO₄ (2500 g) was charged to the reactor containing the organic layer and the mixture was stirred at 20-25° C. for 2 h. The suspension was then filtered through a short pad of Celite (1500 g) then the pad washed with three separate portions of THF (10.0 L). The combined organic layer and washes were then concentrated under vacuum distillation (jacket temperature set to 55° C.). tert-butyl 4-(2-hydroxyethyl-2,2-d₂)piperidine-1-carboxylate was then collected as a yellow oil (1810 g, 100%) in 97.7 A % HPLC purity and used directly in the next step.

Step 3—Benzoylation

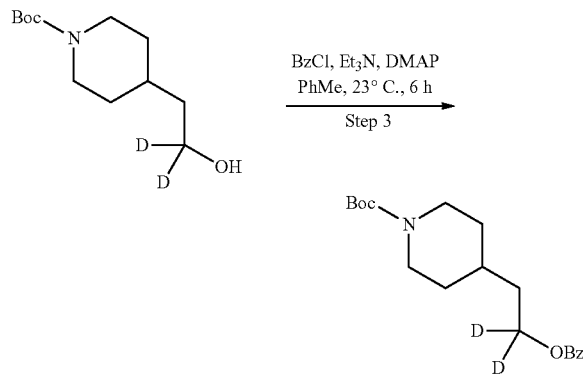

To a reactor under nitrogen equipped with overhead agitation was charged tert-butyl 4-(2-hydroxyethyl-2,2-d$_2$) piperidine-1-carboxylate (2111 g, 9.126 mol, 1.0 equiv), toluene (16.0 L), Et$_3$N (1.9 L, 13.65 mol, 1.5 equiv), and DMAP (109 g, 0.89 mol, 10 mol %). This mixture was stirred then the jacket was cooled to between −5 and 5° C. until the internal temperature achieved <5° C. Benzoyl chloride (1.4 L, 11.027 mol, 1.2 equiv) was charged slowly over 1 h while maintaining the internal temperature <5° C. Upon complete addition of the reagent, the reactor was warmed to 20-30° C. then held for 2 h after reaching the desired jacket temperature. After completion of the reaction was confirmed, a half-saturated NaHCO$_3$ solution (11.8 L) was charged to the reactor and stirred for 10 min. The layers were then separated and the aqueous layer drained to waste. Water (11.8 L) was then charged to the reactor and again stirred for 10 min. The layers were then separated and the aqueous layer drained to waste. The organic layer was then azeotropically dried via vacuum distillation with toluene (5.7 V) with the jacket temperature set to 65° C. The resulting tert-butyl 4-(2-(benzoyloxy)ethyl-2,2-d$_2$)piperidine-1-carboxylate was obtained as a 16.0 V toluene solution in 95.6 A % HPLC purity and then used directly in the next step.

Step 4—Deprotection/Salt Formation

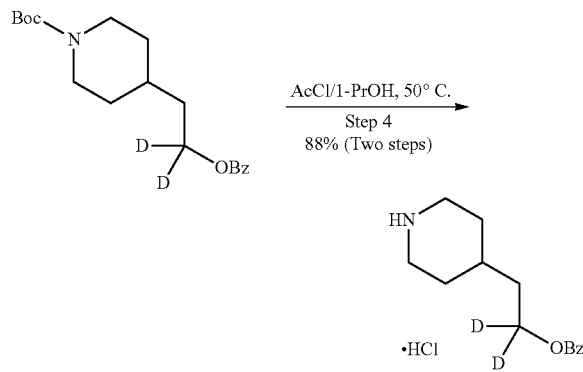

To a reactor under nitrogen equipped with overhead agitation was charged 1-PrOH (5660 mL). The jacket was cooled to 0 to 5° C. then AcCl (2141 mL, 30.08 mol, 3.30 equiv) was charged slowly while maintaining the internal temperature <5° C. (Caution was appropriate as the reaction was exothermic.) Following complete addition of the reagent, the contents were held between 0-5° C. for 30 mins then tert-butyl 4-(2-(benzoyloxy)ethyl-2,2-d$_2$)piperidine-1-carboxylate (3061 g, 9.126 mol, 1.0 equiv) was charged as a toluene solution (16.0 L) then the retaining flask and transfer line were washed forward with toluene (4.0 L). The reactor jacket was then heated to 50° C. and stirred at temperature for 1 h. Upon confirmation of reaction completion, heptane was charged at temperature (jacket 45-55° C.) over 30 min to the self-seeded mixture. Following complete addition of the anti-solvent, the contents were aged for 2 h, the jacket then cooled to 0° C. over 1.5 h, and held at temperature for 1 h. The slurry was then filtered cold and washed with a pre-chilled 15% 1-PrOH: 85% heptane (12.0 L) solution at 0° C. The solids were then dried under vacuum at 25° C. for 48 h to afford 2-(piperidin-4-yl)ethyl-1,1-d$_2$ benzoate hydrochloride as an off-white solid (2188 g, 88% corrected yield over two steps, in 99.7 A % HPLC purity): mp 179-180° C.

$^1$H NMR (400 MHz, DMSO-d$_6$) δ=9.34-8.83 (m, 2H), 8.02-7.92 (m, 2H), 7.70-7.61 (m, 1H), 7.59-7.48 (m, 2H), 3.21 (br d, J=12.5 Hz, 2H), 2.90-2.75 (m, 2H), 1.84 (br d, J=13.4 Hz, 2H), 1.80-1.69 (m, 1H), 1.68-1.63 (m, 2H), 1.50-1.35 (m, 2H). $^{13}$C NMR (101 MHz, DMSO-d$_6$) δ=ppm 166.2, 133.8, 130.2, 129.6, 129.2, 62.2, 43.3, 34.5, 30.8, 28.6.

Step 5—Amide Coupling

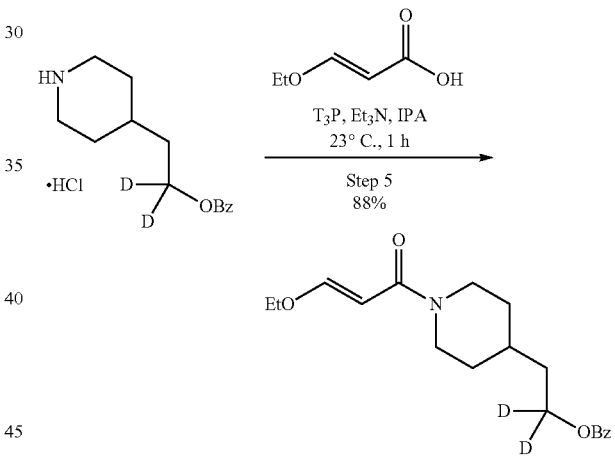

To a reactor under nitrogen equipped with overhead agitation was charged 2-(piperidin-4-yl)ethyl-1,1-d$_2$ benzoate hydrochloride (700 g, 2.576 mol, 1.0 equiv), (E)-3-ethoxyacrylic acid (389 g, 3.35 mol, 1.3 equiv), IPA (3.5 L, 5 V), and Et$_3$N (1.8 L, 12.932 mol, 5.0 equiv). The contents were then stirred at 20-30° C. for 15 min then T3P® (50% solution in EtOAc, 1.85 L, 3.108 mol, 1.2 equiv) was charged slowly over 15 min while maintaining the temperature below 30° C. The reactor jacket was then heated to 40° C. and held at temperature for 1 h. Upon confirmation of reaction completion by HPLC, water (10.5 L) was charged to the reactor over 2 h, then the reactor jacket was cooled to 20-30° C. over 2 h then aged for 12 h. The reaction mixture was filtered and the resulting cake was washed with two portions of a 3:1 mixture of water:IPA (8.0 L). The washed cake was then dried at 45° C. for 44 h and combined with another 700 g reaction conducted identically to the first batch, to afford (E)-2-(1-(3-ethoxyacryloyl)piperidin-4-yl) ethyl-1,1-d$_2$ benzoate as a white solid (1457 g, 87% corrected yield, in 99.3 A % HPLC purity): mp 106-109° C.

$^1$H NMR (400 MHz, DMSO-d$_6$, 60° C.) δ=7.97 (d, J=7.3 Hz, 2H), 7.69-7.62 (m, 1H), 7.56-7.50 (m, 2H), 7.37 (d, J=12.0 Hz, 1H), 5.82 (d, J=11.8 Hz, 1H), 4.17 (br s, 2H), 3.94 (q, J=6.9 Hz, 2H), 2.78 (br s, 2H), 1.81-1.64 (m, 5H), 1.25 (t, J=7.0 Hz, 3H), 1.16-1.01 (m, 2H). $^{13}$C NMR (101 MHz, DMSO-d$_6$, 23° C.) δ=165.2, 164.4, 159.9, 132.6, 129.5, 128.5, 128.1, 95.6, 65.9, 61.5, 42.7, 33.9, 32.2, 31.5, 13.9.

Step 6—Diethyl (1H-benzo[d]imidazol-2-yl)phosphoramidate

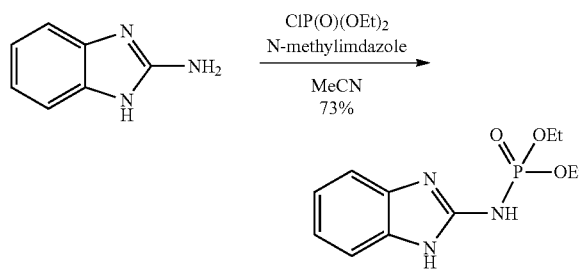

To a reactor under nitrogen was charged 1H-benzo[d]imidazol-2-amine (0.7882 kg, 6.002 mol, 1.00 equiv) followed by MeCN (5.333 L). To this mixture was then added n-methylimidazole (0.6693 kg, 8.103 mol, 1.35 equiv) followed by MeCN (0.460 L) to rinse the reaction vessel. This slurry was then stirred at 20° C. for a minimum of 15 min. Next, ClP(O)(OEt)$_2$ (1.4070 kg, 8.154 mol, 1.35 equiv) was added dropwise over 1 h keeping the internal temperature below 30° C. Upon the completion of the ClP(O)(OEt)$_2$ addition, MeCN (0.455 L) was added to rinse the reaction vessel. This slurry was then stirred at 20° C. for a minimum of 12 h. Upon completion of reaction, the vessel was cooled to 0° C. over a minimum of 30 min and then stirred at this temperature for a minimum of 2 h. This mixture was then filtered and the wetcake was washed with two portions of MeCN (3.2 L). The solids were dried under vacuum at 40° C. for a minimum of 12 h to afford diethyl (1H-benzo[d]imidazol-2-yl)phosphoramidate as an off-white solid (1.2144 kg, corrected yield: 73%, 99.5% HPLC purity): mp 229° C.

$^1$H NMR (400 MHz, Methanol-d$_4$) δ 7.20 (dt, J=7.6, 3.8 Hz, 2H), 7.11 (dd, J=5.9, 3.2 Hz, 2H), 4.07 (p, J=7.2 Hz, 4H), 1.32 (t, J=7.1 Hz, 6H); $^{13}$C NMR (101 MHz, Methanol-d$_4$) δ 123.4, 111.2, 63.4, 63.4, 16.6, 16.6; $^{31}$P NMR (162 MHz, Methanol-d4) δ 7.31.

Step 7—2-(1-(benzo[4,5]imidazo[1,2-a]pyrimidin-2-yl)piperidin-4-yl)ethyl-1,1-d$_2$ benzoate

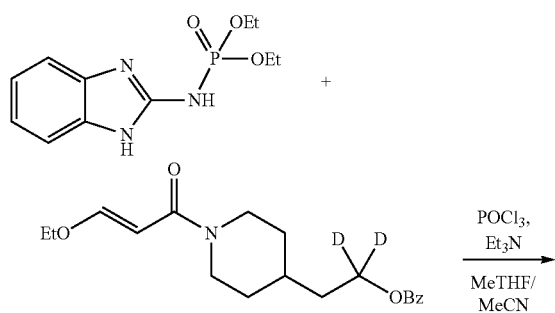

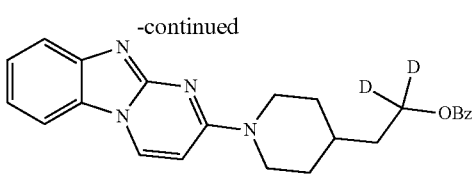

To a reactor under nitrogen was charged MeCN (5.00 L) followed by (E)-2-(1-(3-ethoxyacryloyl)piperidin-4-yl)ethyl-1,1-d$_2$ benzoate (1.00 kg, 3.00 mol, 1.0 equiv) and diethyl (1H-benzo[d]imidazol-2-yl)phosphoramidate (888.5 g, 3.30 mol, 1.1 equiv). MeTHF (5.00 L) was charged followed by Et$_3$N (152.0 g, 1.50 mol, 0.5 equiv). Next, the reactor was cooled between −10 and 10° C. and POCl$_3$ (1.01 kg, 6.60 mol, 2.2 equiv) was added over a minimum 30 min while maintaining the internal temperature between −10 to 10° C. Upon completion of the addition, the contents were then heated to 65-95° C. over a minimum of 2 h and the reaction held at an internal temperature of 80° C. for a minimum of 1.5 h. After completion of reaction was confirmed, the reactor was cooled to 15-25° C. then added to a 25 w/w % solution of K$_2$CO$_3$ (premade by mixing water (5.0 L) with K$_2$CO$_3$ (1.67 kg) and stirring at 20° C. for a minimum of 15 min) over a minimum of 15 min while keeping the internal temperature below 30° C. This was then stirred for a minimum of 15 min after which the layers were separated and the aqueous drained to waste. This reaction solution was then used directly in the next step.

Step 8—2-(1-(benzo[4,5]imidazo[1,2-a]pyrimidin-2-yl)piperidin-4-yl)ethan-1,1-d$_2$-1-ol

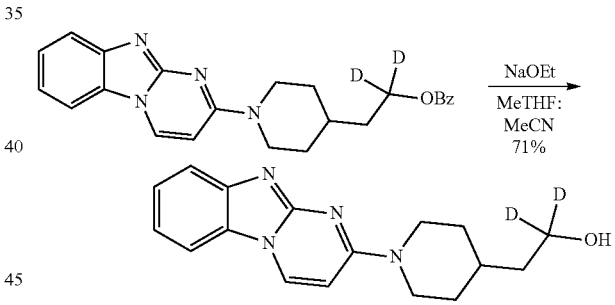

To a reactor under nitrogen containing the crude solution from the previous step was charged a 21 w/w % solution of NaOEt in EtOH (1.90 kg, 6.00 mol). The reactor was then heated to 60-80° C. and stirred for 30-90 min. After reaction completion was confirmed, the mixture was concentrated to 10 L via vacuum distillation. EtOH (10.0 L) was added and a constant-volume distillation was performed while maintaining the internal temperature below 55° C. Water (7.5 L) was then added and the constant-volume distillation was maintained while maintaining the temperature below 60° C. Vacuum was disabled and the solution was cooled to 5° C. over 7 h. An additional charge of a 21 w/w % solution of NaOEt in EtOH was added (300 g, 0.75 mol, 0.25 equiv) and the reaction was heated to 70-80° C. for 1.5 h. After which, the reactor was cooled to 5° C. over the course of 7 h then held at this temperature for a minimum of 2 h. The mixture was filtered and rinsed with a pre-cooled 3:1 water:EtOH solution (4.0 L) at 5-15° C. followed by a wash with water (4.0 L) at 15-25° C. The solids were then dried under vacuum at 40° C. for a minimum of 12 h to afford 2-(1-

(benzo[4,5]imidazo[1,2-a]pyrimidin-2-yl)piperidin-4-yl)ethan-1,1-d$_2$-1-ol as a light-yellow solid (684.0 g, corrected yield: 71%, 97.9% HPLC purity): mp 186° C.

$^1$H NMR (400 MHz, DMSO-d$_6$) δ 8.93 (d, J=7.7 Hz, 1H), 7.93 (d, J=8.0 Hz, 1H), 7.50 (d, J=8.0 Hz, 1H), 7.28 (t, J=7.6 Hz, 1H), 7.13 (t, J=7.6 Hz, 1H), 6.86 (d, J=7.8 Hz, 1H), 4.55 (s, 2H), 4.36 (s, 1H), 2.99 (t, J=12.7 Hz, 2H), 1.82-1.69 (m, 3H), 1.38 (d, J=6.2 Hz, 2H), 1.12 (ddt, J=15.6, 11.8, 6.0 Hz, 2H); $^{13}$C NMR (101 MHz, DMSO-d$_6$) δ 157.8, 152.1, 144.1, 134.2, 127.7, 124.0, 118.9, 117.0, 110.1, 95.8, 44.6, 38.7, 32.1, 31.8.

Step 9—2-(1-(benzo[4,5]imidazo[1,2-a]pyrimidin-2-yl)piperidin-4-yl)ethyl-1,1-d$_2$ 4-methylbenzenesulfonate

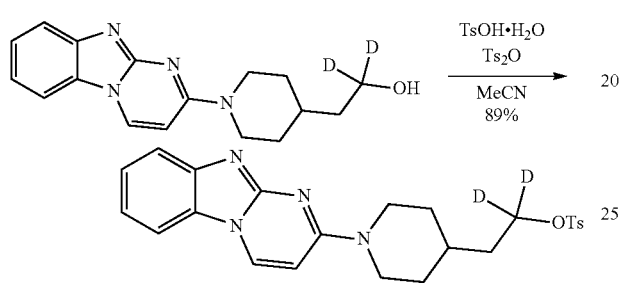

To a reactor under nitrogen was charged 2-(1-(benzo[4,5]imidazo[1,2-a]pyrimidin-2-yl)piperidin-4-yl)ethan-1,1-d$_2$-1-ol (0.6874 kg, 2099 mol, 1.0 equiv) followed by TsOH.H$_2$O (0.531 kg, 2764 mmol. 1.2 equiv). MeCN (3.434 L) was then added and the reaction was stirred for a minimum of 15 min. Next, Ts$_2$O (1.504 kg, 4607 mmol, 2.0 equiv) was added followed by MeCN (0.628 L) to rinse the reaction vessel. This slurry was then stirred at 20° C. for 16 h. After reaction completion was confirmed, H$_2$O (0.687 L) was added. Next, NMP (4.124 L) was added while keeping the internal temperature below 30° C. and following complete addition, the reaction mixture was then stirred for a minimum of 15 min. Meanwhile, in a separate reactor was added a 20 wt % aqueous solution of K$_3$PO$_4$ (6.87 L). Then the crude reaction mixture was added to the basic solution over 1-3 h then the contents aged for a minimum of 1 h. The mixture was then filtered and the wetcake was washed with two portions of water (6.874 L). The solids were dried under vacuum at 20° C. for a minimum of 2 h followed by drying under vacuum at 35° C. for a minimum of 12 h to afford 2-(1-(benzo[4,5]imidazo[1,2-a]pyrimidin-2-yl)piperidin-4-yl)ethyl-1,1-d$_2$ 4-methylbenzenesulfonate as an off-white solid (888.2 g, corrected yield: 89%, 99.3% HPLC purity): mp 151° C.

$^1$H NMR (400 MHz, Chloroform-d) δ 8.23 (d, J=7.8 Hz, 1H), 7.84-7.77 (m, 2H), 7.71 (d, J=8.1 Hz, 1H), 7.55 (d, J=8.0 Hz, 1H), 7.37 (dd, J=7.6, 5.1 Hz, 3H), 7.23-7.14 (m, 1H), 6.40 (d, J=7.8 Hz, 1H), 4.58 (s, 2H), 2.94 (t, J=12.9 Hz, 2H), 2.46 (s, 3H), 1.73 (s, 1H), 1.60 (d, J=6.5 Hz, 2H), 1.18 (qd, J=12.4, 4.1 Hz, 2H); $^{13}$C NMR (101 MHz, Chloroform-d) δ 157.8, 145.1, 132.7, 130.0, 128.0, 127.8, 124.8, 119.8, 118.7, 108.8, 108.8, 95.5, 95.4, 67.9, 45.2, 35.2, 32.5, 31.7, 21.8.

Figure 2:
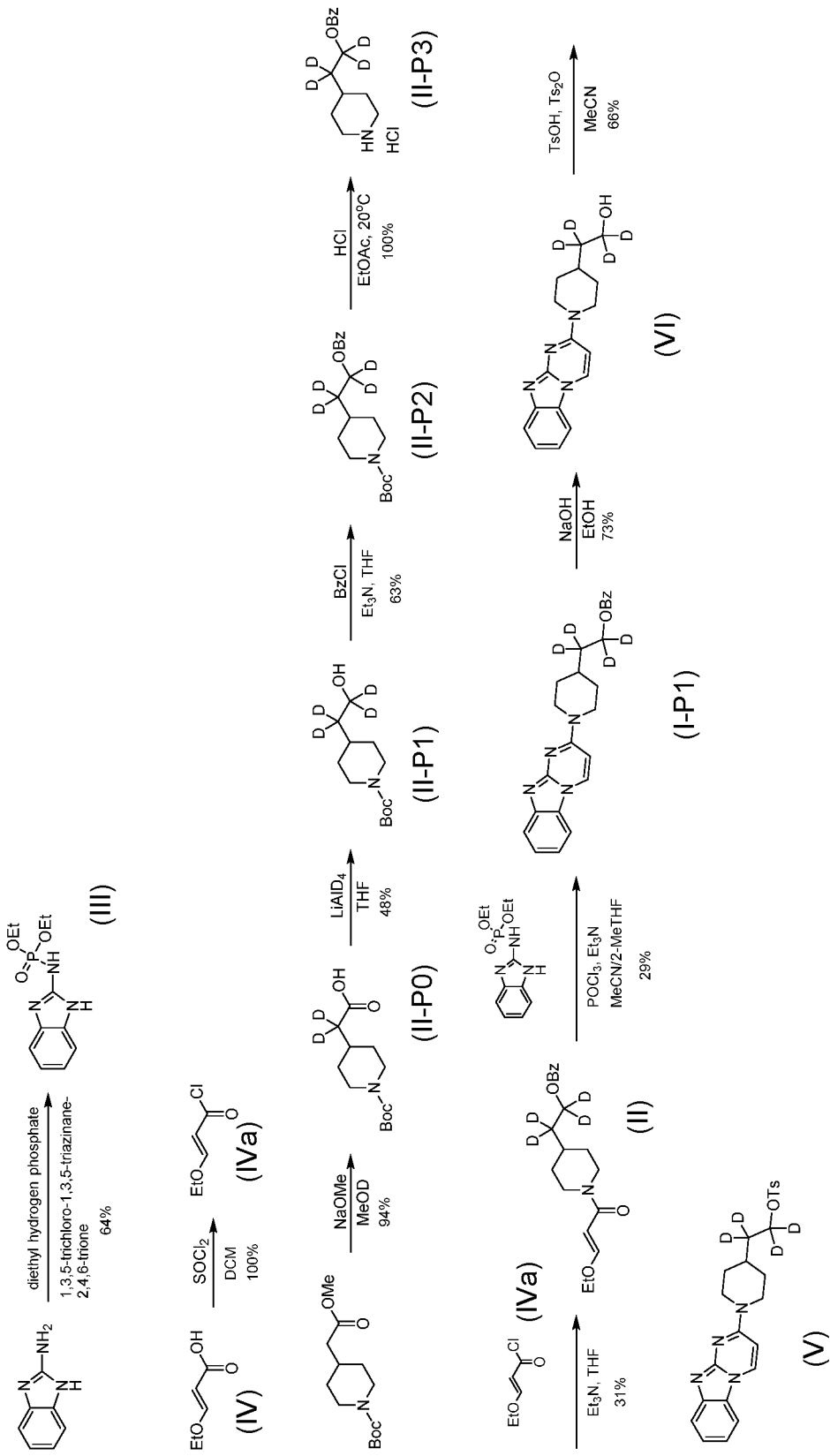
FIG. 2 shows a second flow-chart of a process as described herein.

Example 2: Synthesis of 2-(1-(benzo[4,5]imidazo[1,2-a]pyridin-3-yl)piperidin-4-yl)ethyl-1,1,2,2-d$_4$ 4-methylbenzenesulfonate Example 2 describes a representative synthesis of a tracer molecule that is deuterated at four positions wherein the method uses a step of conjugating an acrylamide with a phosphorylated imidazole. FIG. 2 shows the synthetic pathway in overview, including steps to prepare various starting materials.

Step 1—Preparation of diethyl (1H-benzo[d]imidazol-2-yl)phosphoramidate

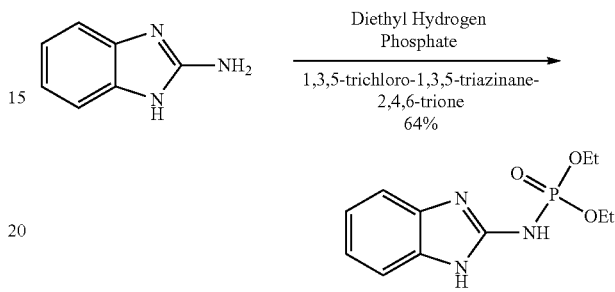

To a flask at 15-25° C. under nitrogen was charged 1,3,5-trichloro-1,3,5-triazinane-2,4,6-trione (5.55 g, 23.8 mmol, 0.31 equiv) and MeCN (35.0 mL). The mixture was stirred until homogenous. Diethyl hydrogen phosphate (10.3 g, 75.1 mmol, 9.69 mL, 1.00 eq) and Et$_3$N (15.2 g, 150.2 mmol, 20.9 mL, 2.00 eq) were then added and the flask was heated to 85° C. and stirred for 30 min, at which point precipitation had occurred. The jacket was then cooled to 0° C. and 1H-benzo[d]imidazol-2-amine (10.0 g, 75.1 mmol, 1.00 equiv), dissolved in THF (35.0 mL), was charged to the flask. The reaction mixture was then warmed to 15-25° C. and stirred for 1 h. Upon confirmation of reaction completion, the reaction was quenched with water (100.0 mL) then extracted with two portions of ethyl acetate (200.0 mL). The combined organic layers were dried over Na$_2$SO$_4$, filtered, and then concentrated under reduced pressure to afford compound diethyl (1H-benzo[d]imidazol-2-yl)phosphoramidate as a brown solid (13.0 g, 48.2 mmol, 64% yield).

$^1$H NMR (400 MHz, CDCl$_3$) δ ppm 7.34 (dd, J=18.03, 7.89 Hz, 2H), 7.19 (td, J=7.67, 1.04 Hz, 1H), 7.05 (td, J=7.70, 0.98 Hz, 1H), 6.13-6.74 (m, 2H), 4.20-4.34 (m, 2H), 4.00-4.19 (m, 3H), 1.33 (td, J=7.09, 0.86 Hz, 6H).

Step 2—Preparation of (E)-3-ethoxyacryloyl Chloride

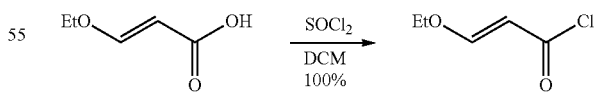

To a solution of (E)-3-ethoxyacrylic acid (4.40 g, 37.8 mmol, 1.00 equiv) in DCM (20.0 mL) was added SOCl$_2$ (4.51 g, 37.8 mmol, 2.75 mL, 1.00 equiv) at 25° C. The mixture was stirred at 40° C. for 1 h. After reaction completion was confirmed, the mixture was evaporated to dryness to afford (E)-3-ethoxyacryloyl chloride as a yellow oil (5.10 g, 37.9 mmol, 100% yield). This was used directly in the next step without purification.

Step 3—2-(1-(tert-butoxycarbonyl)piperidin-4-yl)acetic-2,2-d₂ Acid

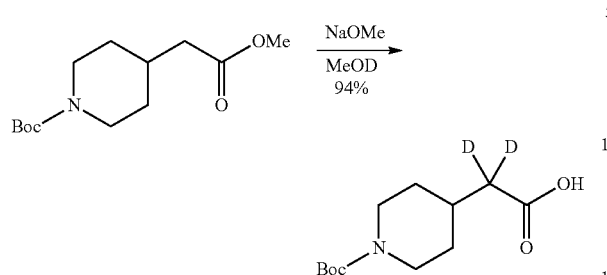

To a solution of tert-butyl 4-(2-methoxy-2-oxoethyl)piperidine-1-carboxylate (28.0 g, 108.8 mmol, 1.00 equiv) in CD₃OD (35.0 mL) at 20° C. under nitrogen was added CD₃ONa (15.5 g, 272.0 mmol, 2.5 equiv) then the reaction was heated to 80° C. for 12 h. After reaction completion was confirmed, the mixture was evaporated to dryness then 1N HCl was added to adjust the pH to a range of 6-7. The resulting mixture was then extracted with three portions of EtOAc (100.0 mL). The organic phases were combined, dried over Na₂SO₄, and then evaporated to dryness. The crude mixture was then purified via flash chromatography (3:1 heptane:ethyl acetate) to afford 2-(1-(tert-butoxycarbonyl)piperidin-4-yl)acetic-2,2-d₂ acid as an off-white solid (25.0 g, 94% yield over two steps).

¹H NMR (400 MHz, CDCl₃) δ ppm 3.96-4.26 (m, 2H), 2.62-2.90 (m, 2H), 1.93 (tt, J=11.63, 3.47 Hz, 1H), 1.73 (br d, J=11.25 Hz, 2H), 1.46 (s, 9H), 1.04-1.31 (m, 2H).

Step 4—tert-butyl 4-(2-hydroxyethyl-1,1,2,2-d₄)piperidine-1-carboxylate

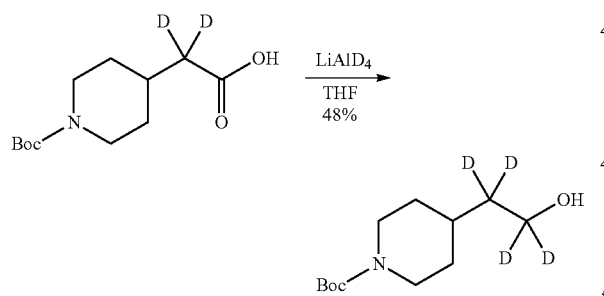

To a solution of LiAlD₄ (8.51 g, 224.2 mmol, 11.5 mL, 2.20 equiv) in THF (175.0 mL) at −10° C. was then slowly added 2-(1-(tert-butoxycarbonyl)piperidin-4-yl)acetic-2,2-d₂ acid (25.0 g, 101.9 mmol, 1.00 equiv) and upon complete addition of the starting material, the mixture was stirred for 10 min. After confirmation of reaction completion, H₂O (8.50 mL) and 15% NaOH (8.50 mL) were added to the reaction. The mixture was then filtered and extracted with three portions of EtOAc (100.0 mL). The organic phases were combined, dried over Na₂SO₄, and evaporated to dryness to afford tert-butyl 4-(2-hydroxyethyl-1,1,2,2-d₄)piperidine-1-carboxylate as a yellow oil (11.5 g, 49.2 mmol, 48% yield).

¹H NMR (400 MHz, CDCl₃) δ ppm 3.98-4.17 (m, 2H), 2.59-2.78 (m, 2H), 1.64-1.73 (m, 2H), 1.53-1.62 (m, 1H), 1.46 (s, 9H), 1.01-1.20 (m, 2H).

Step 5—tert-butyl 4-(2-(benzoyloxy)ethyl-1,1,2,2-d₄)piperidine-1-carboxylate

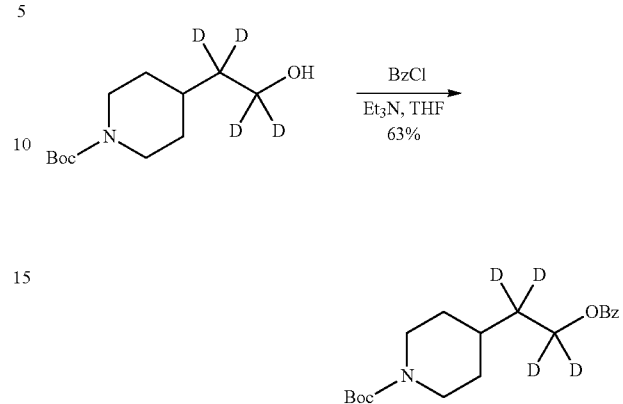

To a solution of tert-butyl 4-(2-hydroxyethyl-1,1,2,2-d₄)piperidine-1-carboxylate (11.5 g, 49.2 mmol, 1.00 equiv), Et₃N (9.97 g, 98.5 mmol, 13.7 mL, 2.00 equiv), and THF (80.5 mL) at 0-10° C. was added BzCl (8.31 g, 59.1 mmol, 6.87 mL, 1.20 equiv) in a dropwise fashion. The mixture was then stirred at 0-10° C. for 1 h. Upon confirmation of reaction completion, H₂O (50.0 mL) was added and the aqueous layer was extracted with three portions of EtOAc (100.0 mL). The organic phases were combined, dried over Na₂SO₄, and evaporated to dryness. The crude was purified by flash chromatography (3:1 petroleum ether:ethyl acetate mobile phase) to afford tert-butyl 4-(2-(benzoyloxy)ethyl-1,1,2,2-d₄)piperidine-1-carboxylate as a yellow oil (10.5 g, 63% yield).

¹H NMR (400 MHz, CDCl₃) δ ppm 8.04 (d, J=7.34 Hz, 2H), 7.52-7.64 (m, 1H), 7.36-7.50 (m, 2H), 4.13 (q, J=7.13 Hz, 2H), 2.71 (br t, J=12.04 Hz, 2H), 1.74 (br d, J=12.84 Hz, 2H), 1.56-1.65 (m, 1H), 1.46 (s, 9H), 1.07-1.23 (m, 2H).

Step 6—2-(piperidin-4-yl)ethyl-1,1,2,2-d₄ benzoate Hydrochloride

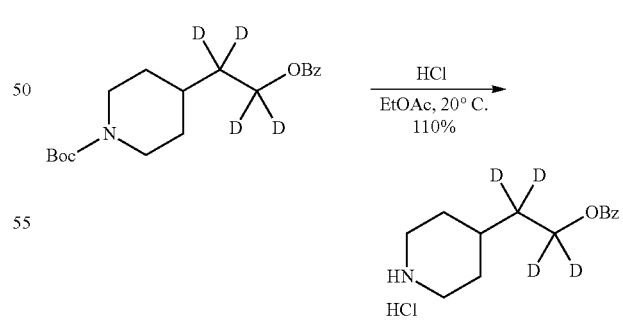

To a solution of tert-butyl 4-(2-(benzoyloxy)ethyl-1,1,2,2-d₄)piperidine-1-carboxylate (10.5 g, 31.1 mmol, 1.00 equiv) in EtOAc (10.5 mL) was added HCl in EtOAc (4 M, 30.0 mL) at 25° C. The mixture was stirred at 25° C. for 1 h and after confirmation of reaction completion, the reaction was evaporated to dryness and the crude was used directly in the next step.

Step 7—(E)-2-(1-(3-ethoxyacryloyl)piperidin-4-yl)ethyl-1,1,2,2-d₄ benzoate

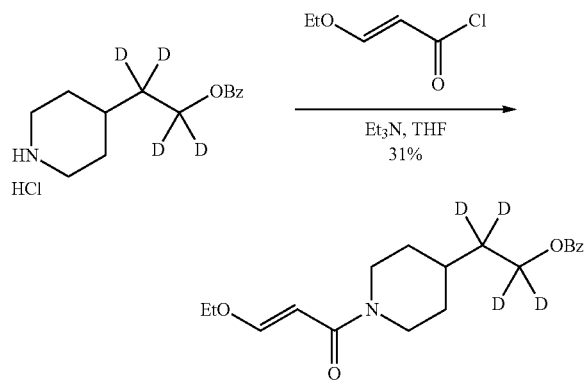

To a solution of 2-(piperidin-4-yl)ethyl-1,1,2,2-d₄ benzoate hydrochloride (8.52 g, 31.1 mmol, 1.00 equiv) and Et₃N (3.15 g, 31.1 mmol, 4.33 mL, 1.00 equiv) in THF (15.0 mL) at 0-10° C. was added the crude (E)-3-ethoxyacryloyl chloride (5.02 g, 37.3 mmol, 1.2 equiv). The reaction was stirred at 0-10° C. for 1 h. Upon confirmation of reaction completion, H₂O (50.0 mL) was added and resulting aqueous was extracted with three portions of EtOAc (50.0 mL). The organic phases were then combined, died over Na₂SO₄, and evaporated to dryness. The residue was then slurried in MTBE (10.0 mL) then filtered to afford (E)-2-(1-(3-ethoxyacryloyl)piperidin-4-yl)ethyl-1,1,2,2-d₄ benzoate (3.20 g, 9.54 mmol, 31% yield) as a yellow solid.

¹H NMR (400 MHz, DMSO-d6) δ ppm 8.03 (br d, J=7.34 Hz, 2H), 7.67-7.78 (m, 1H), 7.51-7.65 (m, 2H), 7.44 (d, J=11.86 Hz, 1H), 5.91 (d, J=11.86 Hz, 1H), 4.09-4.60 (m, 2H), 3.93-4.03 (m, 2H), 2.66-3.12 (m, 2H), 1.61-1.89 (m, 3H), 1.29 (t, J=7.03 Hz, 3H), 1.00-1.18 (m, 2H).

Step 8—2-(1-(benzo[4,5]imidazo[1,2-a]pyrimidin-2-yl)piperidin-4-yl)ethyl-1,1,2,2-d₄ benzoate

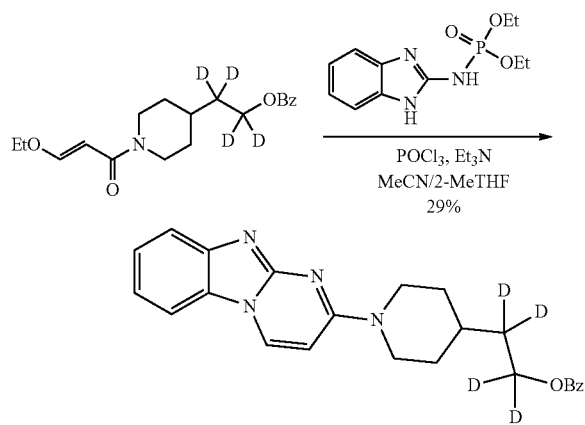

To a solution of diethyl (1H-benzo[d]imidazol-2-yl)phosphoramidate (2.30 g, 8.53 mmol, 1.10 equiv) and (E)-2-(1-(3-ethoxyacryloyl)piperidin-4-yl)ethyl-1,1,2,2-d₄ benzoate (2.60 g, 7.75 mmol, 1.00 equiv) in 2-MeTHF (13.0 mL) and MeCN (13.0 mL) at 25° C. was added Et₃N (392 mg, 3.88 mmol, 539 μL, 0.50 equiv.) followed by POCl₃ (2.61 g, 17.0 mmol, 1.58 mL, 2.20 equiv). The reaction was then heated to 80° C. and stirred for 4 h. Upon confirmation of reaction completion, saturated aqueous NaHCO₃ (100.0 mL) was charged and the resulting aqueous layer was extracted with three portions of DCM (100.0 mL). The organic phases were then combined, died over Na₂SO₄, and evaporated to dryness. The crude was then slurried in EtOAc (30.0 mL) then filtered. This slurry process was repeated twice more. The resulting solids were then purified by prep-HPLC to afford 2-(1-(benzo[4,5]imidazo[1,2-a]pyrimidin-2-yl)piperidin-4-yl)ethyl-1,1,2,2-d₄ benzoate (0.900 g, 2.22 mmol, 29% yield) as a yellow solid.

¹H NMR (400 MHz, DMSO-d6) δ ppm 8.94 (d, J=7.82 Hz, 1H), 7.89-8.03 (m, 3H), 7.61-7.72 (m, 1H), 7.45-7.58 (m, 3H), 7.24-7.34 (m, 1H), 7.07-7.19 (m, 1H), 6.89 (d, J=7.82 Hz, 1H), 4.39-4.82 (m, 2H), 3.03 (br t, J=11.55 Hz, 2H), 1.74-1.96 (m, 3H), 1.05-1.34 (m, 2H).

¹³C NMR (400 MHz, DMSO-d6) δ ppm 166.2, 158.3, 152.5, 144.6, 134.8, 133.7, 130.3, 129.5, 129.2, 128.2, 124.5, 119.4, 117.5, 110.6, 96.3, 44.9, 32.9, 32.0.

Step 9—2-(1-(benzo[4,5]imidazo[1,2-a]pyrimidin-2-yl)piperidin-4-yl)ethan-1,1,2,2-d₄-1-ol

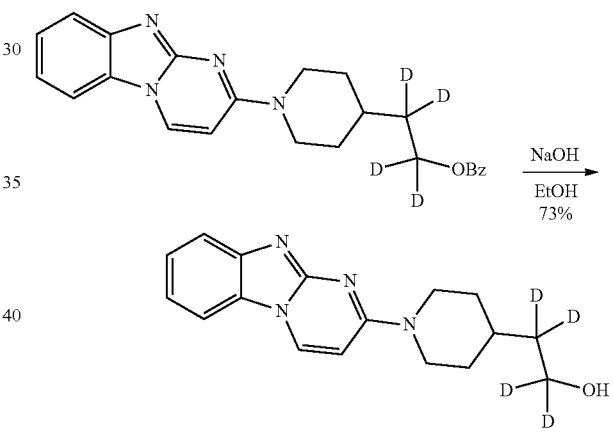

To a solution of 2-(1-(benzo[4,5]imidazo[1,2-a]pyrimidin-2-yl)piperidin-4-yl)ethyl-1,1,2,2-d₄ benzoate (0.900 g, 2.22 mmol, 1.00 equiv) in EtOH (10.0 mL) at 25° C. was added 5N NaOH (889.9 mg, 4.45 mmol, 2.00 equiv). The reaction was heated at 70° C. for 1 h. Upon confirmation of reaction completion, H₂O (100.0 mL) was added and the aqueous layer was extracted with three portions of DCM (100.0 mL). The organic phases were then combined, died over Na₂SO₄, and evaporated to dryness. The crude was then slurried in MTBE (30.0 mL) and filtered to afford 2-(1-(benzo[4,5]imidazo[1,2-a]pyrimidin-2-yl)piperidin-4-yl)ethan-1,1,2,2-d₄-1-ol (500 mg, 1.63 mmol, 73% yield) as a yellow solid.

¹H NMR (400 MHz, DMSO-d6) δ ppm 8.93 (d, J=7.70 Hz, 1H), 7.93 (d, J=7.95 Hz, 1H), 7.49 (d, J=7.95 Hz, 1H), 7.28 (t, J=7.58 Hz, 1H), 7.08-7.17 (m, 1H), 6.87 (d, J=7.70 Hz, 1H), 4.47-4.73 (m, 2H), 4.36 (br s, 1H), 2.99 (br t, J=11.62 Hz, 2H), 1.63-1.90 (m, 3H), 1.00-1.24 (m, 2H).

13C NMR (400 MHz, DMSO-d6) δ ppm 158.3, 152.5, 144.6, 134.7, 128.2, 124.5, 119.4, 117.5, 110.6, 96.3, 45.2, 32.5, 32.2.

Step 10—2-(1-(benzo[4,5]imidazo[1,2-a]pyrimidin-2-yl)piperidin-4-yl)ethyl-1,1,2,2-d₄ 4-methylbenzenesulfonate

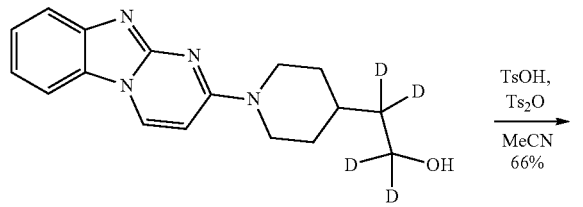

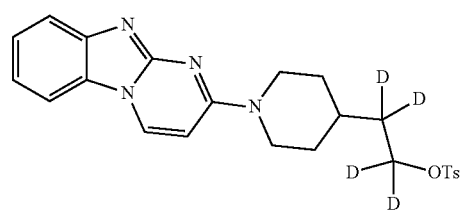

To a solution of 2-(1-(benzo[4,5]imidazo[1,2-a]pyrimidin-2-yl)piperidin-4-yl)ethan-1,1,2,2-d₄-1-ol (500 mg, 1.66 mmol, 1.00 equiv) and TsOH.H₂O (380 mg, 2.00 mmol, 1.20 equiv) in MeCN (3.00 mL) at 25° C. was charged 4-methylbenzenesulfonic anhydride (1.09 g, 3.33 mmol, 2.00 equiv). The reaction was heated to 40° C. and stirred for 12 h. Upon confirmation of reaction completion, H₂O (0.500 mL) and NMP (3.00 mL) were added. A 20 w % solution of aqueous K₃PO₄ (5.00 mL) was then added and the resulting mixture was stirred at 25° C. for 2 h. After aging, the mixture was filtered and the cake washed with three portions of H₂O (5.00 mL). The cake was then slurried in MTBE (10.0 mL) and filtered to give 2-(1-(benzo[4,5]imidazo[1,2-a]pyrimidin-2-yl)piperidin-4-yl)ethyl-1,1,2,2-d₄ 4-methylbenzenesulfonate (500 mg, 1.10 mmol, 66% yield, 96.9% purity) as an off-white solid.

¹H NMR (500 MHz, DMSO-d₆) δ 9.18 (d, J=7.8 Hz, 1H), 8.16 (d, J=8.1 Hz, 1H), 7.79 (d, J=8.0 Hz, 2H), 7.57 (d, J=7.9 Hz, 1H), 7.52 (t, J=7.4 Hz, 1H), 7.47 (m, 3H), 7.31 (d, J=7.9 Hz, 1H), 4.81 (d, J=13.2 Hz, 1H), 4.32 (d, J=13.9 Hz, 1H), 3.23 (t, J=12.5 Hz, 1H), 3.01 (t, J=13.3 Hz, 1H), 2.41 (s, 3H), 1.73 (m, 1H), 1.70 (m, 2H), 1.11 (m, 2H); ¹³C NMR (126 MHz, DMSO-d₆) δ 159.0, 148.1, 145.3, 135.8, 132.9, 130.5, 128.0, 127.2, 126.0, 123.6, 112.5, 112.1, 100.3, 68.3, 46.7, 44.5, 33.5, 31.6, 31.1, 21.4. HRMS m/z ([M+H]+) calculated for C₂₄H₂₂D₄N₄O₃S 455.2050. found 455.2056.

All references cited herein are incorporated by reference in their entireties.

The foregoing description is intended to illustrate various aspects of the instant technology. It is not intended that the examples presented herein limit the scope of the appended claims. The invention now being fully described, it will be apparent to one of ordinary skill in the art that many changes and modifications can be made thereto without departing from the spirit or scope of the appended claims.

What is claimed:

1. A compound of formula:

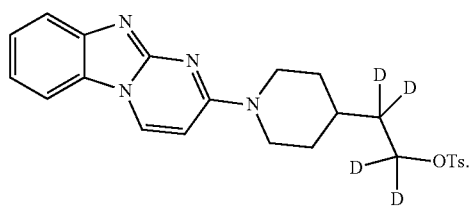 [SMILES: [2H]C([2H])(OS(=O)(=O)c1ccc(C)cc1)C([2H])([2H])C1CCN(c2ccn3c(n2)nc2ccccc23)CC1]

2. The compound of claim 1, having a deuterium enrichment factor of 3,000 or greater at each deuterium atom.

3. A compound of formula:

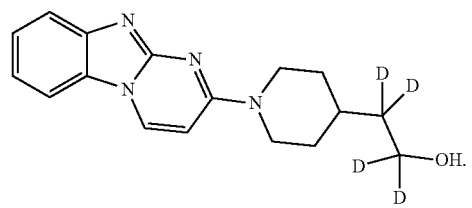 [SMILES: [2H]C([2H])(O)C([2H])([2H])C1CCN(c2ccn3c(n2)nc2ccccc23)CC1]

4. The compound of claim 3, having a deuterium enrichment factor of 3,000 or greater at each deuterium atom.

5. A method of synthesizing the compound of formula (I), the method comprising:

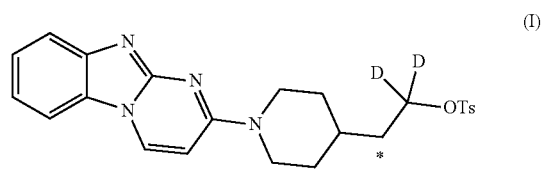

(I)

coupling a compound of formula (II) with a compound of formula (III)

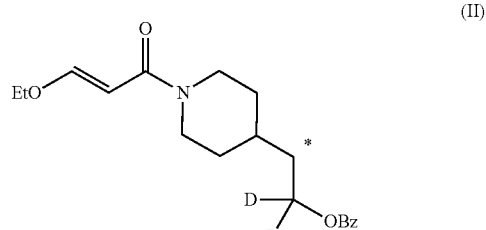

(II)

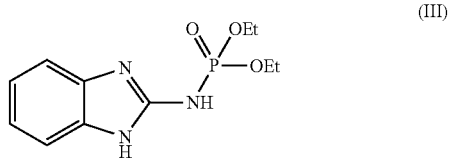

(III)

in the presence of POCl₃ and Et₃N in a non-aqueous solvent to give a first precursor (I-P1);

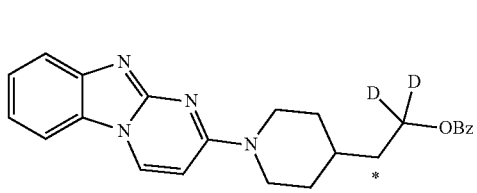
(I-P1)

removing the benzoate group in I-P1 to give second precursor (I-P2); and

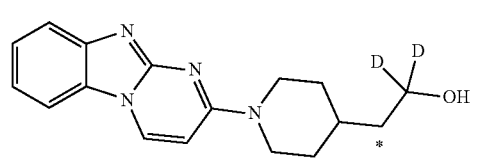
(I-P2)

replacing the hydroxyl group in I-P2 by a tosyl group to give compound (I),
wherein, in formulae (I), (II), (I-P1) and (I-P2), the carbon atom labeled (*) is optionally doubly-deuterated.

6. The method of claim 5, wherein the compound of formula (II) is synthesized by a method comprising:
reacting

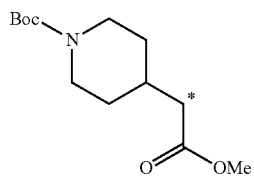 [SMILES: COC(=O)CC1CCN(C(=O)OC(C)(C)C)CC1]

with a first deuterating agent to produce a compound of formula (II-P1);

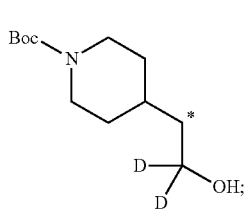
(II-P1)

introducing a benzoyl group to the hydroxyl group of (II-P1) to produce a compound of formula (II-P2);

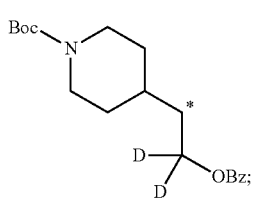
(II-P2)

removing the Boc protecting group from (II-P2) to produce a hydrochloride salt (II-P3); and

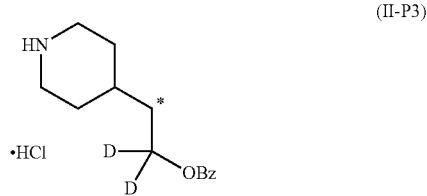
(II-P3)

reacting (II-P3) with

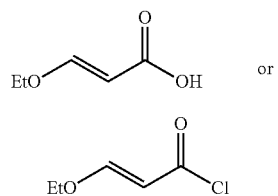
(IV)

or (IVa)

to produce the compound of formula (II).

7. The method of claim 6, wherein the first deuterating agent comprises $LiAlD_4$.

8. The method of claim 6, wherein the first deuterating agent comprises $D_2$ gas.

9. The method of claim 6, wherein compound (IVa) is formed by reacting

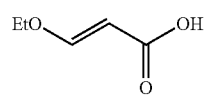

with $SOCl_2$.

10. The method of claim 6, wherein the carbon atom labeled (*) is doubly deuterated, and wherein compound (II-P1) is created by:
reacting

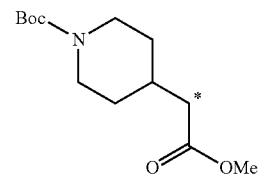 [SMILES: COC(=O)CC1CCN(C(=O)OC(C)(C)C)CC1]

with a second deuterating agent to produce a compound of formula (II-P0); and

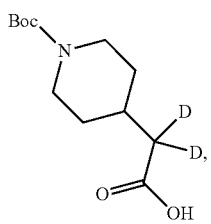

reacting the first deuterating agent with (II-P0) to form $d_4$-(II-P1).

11. The method of claim 5 wherein the compound of formula (III) is synthesized by a method comprising:
reacting

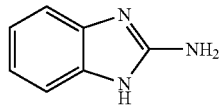

with PCl(O)(OEt)$_2$, in the presence of N-methylimidazole, and MeCN.

12. The method of claim 11, wherein the PCl(O)(OEt)$_2$ is formed in situ by reacting diethyl hydrogen phosphate with 1,3,5-trichloro-1,3,5-triazinane-2,4,6-trione.

13. The method of claim 11, wherein the compound of formula (III) is formed by:
charging a reactor under nitrogen with

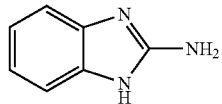

and MeCN;
adding N-methylimidazole followed by MeCN to the mixture; and
adding ClP(O)(OEt)$_2$ dropwise for 1 hour at a temperature between 20 and 30° C.

14. The method of claim 11, wherein the compound of formula (III) is formed by:
charging a flask under nitrogen with 1,3,5-trichloro-1,3,5-triazinane-2,4,6-trione and MeCN;
adding diethyl hydrogen phosphate and Et$_3$N to the flask;
cooling the flask to 0° C. and adding 1H-benzo[d]imidazol-2-amine dissolved in THF; and
warming the reaction mixture to 15-25° C. for 1 hour.

15. The compound of claim 1, having a deuterium enrichment factor of 4,000 or greater at each deuterium atom.

16. The compound of claim 3, having a deuterium enrichment factor of 4,000 or greater at each deuterium atom.

17. The method of claim 5, further comprising radiolabeling the compound of formula (I) by replacing the tosylate group with an $^{18}$F atom.

18. The method of claim 5, wherein the removing the benzoate group from compound (I-P1) occurs in the presence of NaOEt and EtOH.

19. The method of claim 18, wherein the removing takes place in a reactor under nitrogen.

20. The method of claim 5, wherein the replacing the hydroxyl group in compound (I-P2) with a tosyl group additionally includes basification after reacting (I-P2) with tosylate.

21. The method of claim 20, wherein:
the reacting with tosylate occurs in a reactor under nitrogen in a solvent mixture comprising MeCN and NMP; and
the basification is carried out with K$_3$PO$_4$.

22. The method of claim 5, wherein the coupling of the compound of formula (II) with the compound of formula (III) comprises:
charging a reactor under nitrogen with MeCN followed by compound (II) and compound (III);
adding MeTHF and Et$_3$N to the reactor;
cooling the reactor to between -10 and 10° C.;
adding POCl$_3$ to the reactor;
heating the contents of the reactor to 65-95° C. over a minimum of 2 hours;
maintaining the contents of the reactor at 80° C. for at least 1.5 hours;
cooling the contents to 15-25° C. and adding 25 w/w% solution of K$_2$CO$_3$.

23. The method of claim 5, wherein the carbon atom labeled (*) is doubly deuterated, and wherein removing the benzoate group from d$_4$-(I-P1) comprises:
adding NaOH to a solution of d$_4$-(I-P1).

24. The method of claim 5, wherein the carbon atom labeled (*) is doubly deuterated, and wherein the replacing the hydroxyl group in d$_4$-(I-P2) by a tosyl group to give compound d$_4$-(I), comprises:
adding 4-methylbenzenesulfonic anhydride to a solution of d$_4$-(I-P2) and TsOH•H$_2$O in MeCN; and
heating the mixture to 40 ° C.

25. The method of claim 6, wherein the compound

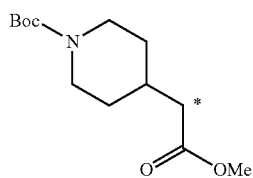 [SMILES: COC(=O)CC1CCN(C(=O)OC(C)(C)C)CC1]

is purified by a method comprising passing the compound over charcoal, filtering and drying the resulting oil.

26. The method of claim 6, wherein the introducing a benzoyl group to the hydroxyl group of (II-P1) comprises:
charging compound (II-P1) to a reactor under nitrogen, with toluene, Et$_3$N, DMAP, and benzoyl chloride at a temperature between -5 and 5° C.

27. The method of claim 6, wherein the removing the Boc protecting group from (II-P2) comprises:
charging a reactor under nitrogen at 0-5° C. with AcCl and 1-PrOH, compound (II-P2) in toluene solution; and
heating the mixture to 50 ° C. for 1 hour.

28. The method of claim 6, wherein the reacting (II-P3) with (IV) comprises:
charging a reactor under nitrogen at 20-30° C. with compound (II-P3), (E)-3-ethoxyacrylic acid (IV), and Et$_3$N; and
heating the mixture to 40° C. for 1 hour.

29. The method of claim 6, wherein the compound of formula (II) is formed by reacting (II-P3) with (IVa), and (IVa) is formed by reacting (IV) with SOCl$_2$ in DCM.

30. The method of claim 6, wherein the carbon atom labeled (*) is doubly deuterated, and wherein compound (II-P2) is created by:
adding BzCl to a solution of II-P1 in Et$_3$N and THF at 0-10° C. for 1 hour.

31. The method of claim 6, wherein the carbon atom labeled (*) is doubly deuterated, and wherein the removing the Boc protecting group from compound (II-P2) comprises:
adding HCl in EtOAc to a solution of (II-P2) in EtOAc.

32. The method of claim 6, wherein the carbon atom labeled (*) is doubly deuterated and the reacting d$_4$-(II-P3) with (IVa) comprises:
adding (IVa) to d$_4$-(II-P3) in ET$_3$N amd THF at 0-10° C. for 1 hour.

33. The method of claim 6, wherein the carbon atom labeled (*) is doubly deuterated and the coupling of the compound of formula (II) with the compound of formula (III) comprises:

forming a solution of compound (III) and d₄-(II) in 2-MeTHF and MeCN;
adding Et₃N followed by POCl₃ to the solution;
heating the solution to 80 ° C. for 4 hours; and
adding NaHCO₃ to the solution.

34. The method of claim 7, wherein a reactor under nitrogen was charged with anhydrous THF, the compound

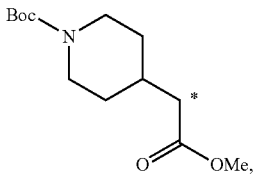

and LiAlD₄ at 0-5 ° C. for 1 hour.

35. The method of claim 8, wherein the deuterium gas was applied to a pressure reactor containing compound

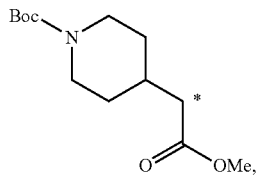

NaOMe, RuMACHO®, and PhMe, at a temperature of 100° C., and a pressure of 20 atmospheres for 24 hours.

36. The method of claim 10, wherein the second deuterating agent is CD₃ONa in CD₃OD, and the reacting with the second deuterating agent takes place at 80° C. for 12 hours.

37. The method of claim 10, wherein the first deuterating agent is LiAlD₄ in THF, and the reacting takes place at -10° C.

38. A composition comprising a compound of formula (I), wherein the di-deuterated compound is present at an isotopic purity of >95% relative to non-deuterated and mono-deuterated forms.

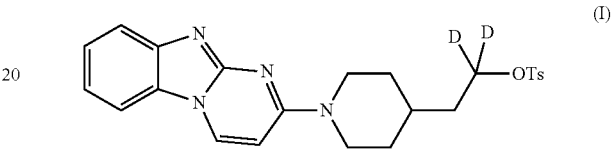

* * * * *